United States Patent [19]
Butler et al.

[11] Patent Number: 5,358,853
[45] Date of Patent: Oct. 25, 1994

[54] LIQUID THROMBOPLASTIN REAGENT

[75] Inventors: James R. Butler, Chapel Hill; Juan L. Torres, Durham; Rajesh Sharma, Cary, all of N.C.

[73] Assignee: Akzo AV, Arnhem, Netherlands

[21] Appl. No.: 924,211

[22] Filed: Aug. 3, 1992

[51] Int. Cl.$^5$ .................. C12Q 1/56; C12Q 1/34; G01N 33/48; G01N 1/00
[52] U.S. Cl. .................. 435/13; 435/18; 435/63; 435/68.1; 435/810; 435/212; 435/226; 424/2; 536/18.7; 436/63; 436/69
[58] Field of Search .................. 435/13, 18, 810, 63, 435/69; 514/21; 436/69, 63; 536/18.7; 424/2

[56] References Cited
U.S. PATENT DOCUMENTS

| | | | |
|---|---|---|---|
| 2,516,216 | 7/1950 | Kazal | 435/13 |
| 2,842,480 | 7/1958 | Singher et al. | 436/69 |
| 2,847,347 | 8/1958 | Singher et al. | 436/69 |
| 2,847,350 | 8/1958 | Singher et al. | 436/69 |
| 2,921,000 | 1/1960 | Singher et al. | 436/69 |
| 3,522,148 | 7/1970 | Adam, Jr. et al. | 435/13 |
| 4,416,812 | 11/1983 | Becker | 435/13 |
| 4,458,015 | 7/1984 | Jering et al. | 435/13 |
| 4,755,461 | 7/1988 | Lawson et al. | 435/13 |
| 5,091,304 | 2/1992 | LaDuca et al. | 435/13 |

OTHER PUBLICATIONS

Day et al, NCCLS Document H28-T, vol. 12 No. 22, pp. 1-14 (1992). (NCCLS is National Committee for Clinical Lab Standards).

Z. Boda et al., "Thromboplastin reagent for prothrombin time determination" *Chemical Abstracts*, vol. 112, No. 11, Mar. 12, 1990, Abstract No. 95033f, USA.

S. Kitchen et al., "A method for the determination of activated factor VII using bovine and rabbit brain thromboplastins: demonstration of increased levels on disseminated intravascular coagulation" *Chemical Abstracts*, vol. 109, No. 1, Jul. 4, 1988, Abstract No. 2785c, USA.

G. Palareti et al. "Use of a new rabbit brain thromboplastin reagent (Thromboplastin FS) in the coagulation laboratory" *Chemical Abstracts*, vol. 104, No. 15, Apr. 14, 1986, Abstract No. 12602x, USA.

*Primary Examiner*—Jeffrey E. Russel
*Assistant Examiner*—Louise N. Leary
*Attorney, Agent, or Firm*—Mary E. Gormley; William M. Blackstone

[57] ABSTRACT

The invention is a stable liquid thromboplastin reagent used for measuring the performance of the coagulation system, with a shelf life of greater than 16 months, and a method of producing this reagent.

7 Claims, 9 Drawing Sheets

LIQUID THROMBOPLASTIN REAGENT

BACKGROUND OF THE INVENTION

This invention relates to a stable liquid thromboplastin reagent with a long shelf-life and a method of producing it.

The operation of the coagulation and fibrinolysis pathways of the blood system can be tested at many stages for abnormalities. One of the most commonly used tests is the prothrombin time test (PT). A sample of blood or plasma is added to thromboplastin in the presence of calcium, and the time needed to form a clot is measured. Factor VII is activated by the thromboplastin, which through factors V and X, causes the formation of thrombin from prothrombin (Factor II). The thrombin formed cleaves fibrinogen to insoluble fibrin. The time measured from the mixing of thromboplastin and calcium with a blood sample to the formation of a clot is a measure of the concentration or activity of the coagulation factors involved. This test is used to monitor oral anticoagulant therapy in order to insure that the proper amount of anticoagulant is given the patient. It is also used to test the performance of the coagulation system.

Thromboplastin is the primary reagent for the above tests. Currently, it is obtained from mammalian tissue, usually rabbit brains. Other thromboplastin-rich tissue, such as human brain, human placenta and bovine brain can be used, but is has been found that for cost, performance and availability, rabbit brain tissue is a suitable source of thromboplastin.

The sensitivity of a thromboplastin reagent rests on a number of factors, such as the final reagent composition, which may include buffers, salts and stabilizers; the method of extracting the thromboplastin from tissue; and the original source of the tissue. Most of the prepared thromboplastin reagents on the market today are only available as lyophilized materials, primarily for reasons of reagent stability. Reconstituted lyophilized thromboplastin reagent has a shelf life of approximately four days.

Stability of this reagent is important to the clinician, or user, as it is expensive and the longer the shelf life, both of the opened and unopened reagent container, the less reagent that must be discarded due to expired shelf-life time.

There are inherent problems associated with a lyophilized product that are either reduced or eliminated in a liquid product. These include (1) variability in the filling of the vials before lyophilization; (2) shelf-to-shelf, and shelf positional differences in the lyophilization cycle (freezing and heating); (3) pipette errors associated with reconstitution and/or wrong volume additions when reconstituting the powder; and (4) water used to reconstitute may not be pure and/or may be contaminated with microorganisms.

A lyophilized reagent is inherently more turbid than a liquid reagent. Reducing turbidity of the reagent is also an important factor in producing a better reagent as the clot must be detected as soon as it forms in the PT test.

There are many ways to extract thromboplastin from tissues. The most common is to extract the thromboplastin-rich tissue in water or saline solutions at 25°-50° C. A saline-tartrate solution can be used, after which the extract is centrifuged to remove large particles. The supernatant contains the active thromboplastin along with sodium chloride and sodium tartrate (U.S. Pat. No. 3,522,148). This extract can be further processed. For example, calcium lactate, glycine, carboxymethylcellulose and imidazole can be added to the thromboplastin extract. Each additive has an effect on the sensitivity of the reagent. In general, an acceptable thromboplastin reagent must produce a PT of 9-15 seconds with a normal blood sample.

There are also a number of other processes used to manufacture more sensitive rabbit brain thromboplastin. Hawkins et al., in WO 90/05740, published on May 31, 1990, disclose a method of extracting thromboplastin from tissue using barium sulfate, chaotropic agents and nonionic detergents. However, the process produces only a lyophilized thromboplastin reagent and not a liquid one.

Another patent application, DE 3150594A1, discloses a similar process. Rabbit brain powder is mixed with cellulose powder and washed with sodium acetate buffer at Ph 6.5-8 to remove contaminants. It is then extracted with surfactants in the presence of calcium ions. Again, the thromboplastin produced is stable only in lyophilized form, with a short shelf life once it has been reconstituted.

A liquid thromboplastin is currently available from Pacific Hemostasis, Inc. Although it would appear that this reagent has overcome some problems associated with lyophilized reagents, it is not available as a single vial reagent. Two solutions, in separate vials must be combined to yield a reagent with only a one month stability.

Therefore, in terms of convenience, stability and reliability, a liquid thromboplastin reagent would be of value to the clinical and research laboratories.

BRIEF SUMMARY OF THE INVENTION

The present invention is a liquid thromboplastin reagent composed of thromboplastin tissue extract, calcium ions, stabilizers and antimicrobials. This reagent has a shelf life, in the unopened final container, of at least 16 months and once opened, of at least 10 days.

Also claimed is a method for producing this liquid thromboplastin reagent, the steps being:
 a) cleaning the thromboplastin-rich tissue, such as rabbit brain acetone powder (RBAP) to remove extraneous, primarily non-thromboplastin containing matter;
 b) extracting the thromboplastin from the cleaned RBAP by mixing with extraction solution at temperatures that are conducive to extraction of thromboplastin;
 c) diluting the thromboplastin-containing supernatant with albumin and calcium ions under conditions favorable to the formation of stable vesicles or micelies;
 d) stabilizing the solution of step c) further by adjusting the pH;
 e) adding antimicrobial agents to the solution;
 f) additionally stabilizing the solution by adding PEG;
 g) testing the solution for prothrombin time (PT) values, and, if needed;
 h) adjusting PT values.

This method of preparing a thromboplastin reagent is an improvement in the art of producing such reagent in liquid form, not lyophilized or reconstituted, and with a maximized shelf-life, through the combined effect of a number of parameters.

DETAILED DESCRIPTION OF THE INVENTION

The present invention is a stable liquid thromboplastin reagent, composed of tissue acetone powder extract, calcium ions, stabilizers and antimicrobial reagents, having a shelf life in an unopened container of at least 16 months.

Although a number of tissue sources can be used from which thromboplastin can be extracted, such as human brain and placenta, currently rabbit brain is the common choice. Rabbit brain tissue is commonly available as an acetone powder extract. Some sources of the powder include Continental Services Group, Inc. (P.O. Box 420-950, 1300 N.W. 36th Street, Miami, Fla., USA 33142) and Pel Freeze Biologicals (P.O. Box 68, 205 N. Arkansas, Rogers, Ark. 72556). It is generally prepared by the method of F. A. Pitlick et al., Methods in Enzymology, Vol. XLV, Part B, edited by L. Lorand, p. 37, 1976.

Once the rabbit brain has been processed to the powder form, various factors affect the extraction of thromboplastin from it. In particular, time and temperature of extraction, the mixing rate, the ionic strength, and the concentration of RBAP all affect the amount and quality of extracted thromboplastin.

The level of thromboplastin activity in RBAP extracts can be estimated using a spectrophotometric assay. The assay can be used to estimate the thromboplastin concentration of the extracts against a reference lot. A series of dilutions of a reference thromboplastin lot is first prepared using a defined sample buffer, which contains 25 mM calcium gluconate, 50 mM sodium chloride, and 25 mM Hepes buffer, pH 7. The clotting rate of normal plasma is determined using these dilutions from clotting curves generated at 405 nm (i.e., maximum $\Delta A/min$.). A dilution of the unknown thromboplastin extract is analyzed in the same way and the concentration is determined in relation to the reference thromboplastin lot.

In a typical assay, a 0.1 ml aliquot of a given dilution of reference or test sample is added to 1 ml of buffer in a 2.9 ml microcuvette. The reaction is carried out at 37° C. and started with the addition of 0.35 ml of normal pooled plasma. The change in absorbance at 405 nm as a function of time is determined using a spectrophotometer.

Figure 1:
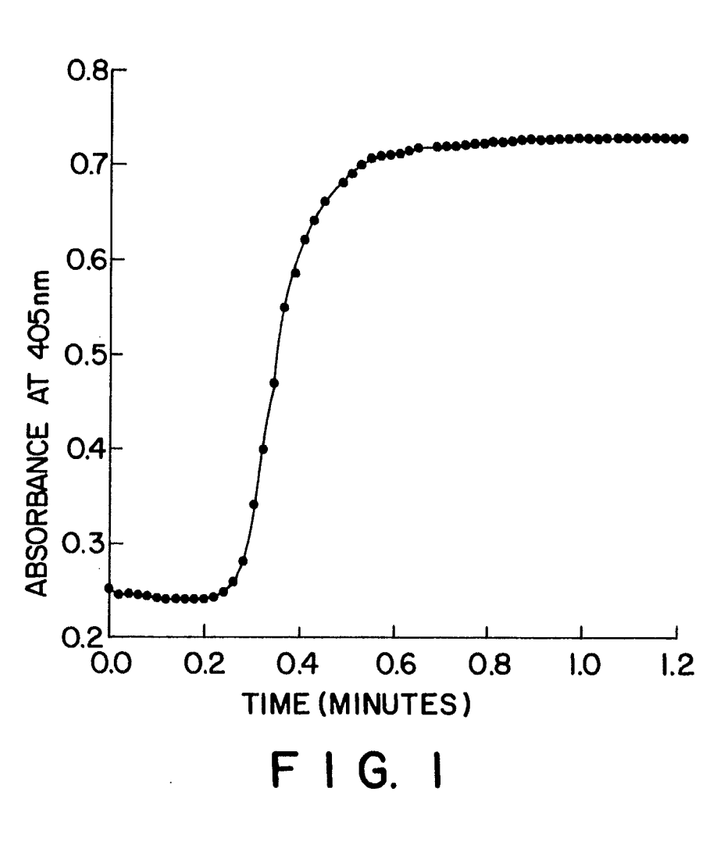
FIG. 1 is a typical thromboplastin assay progress curve.
Figure 2:
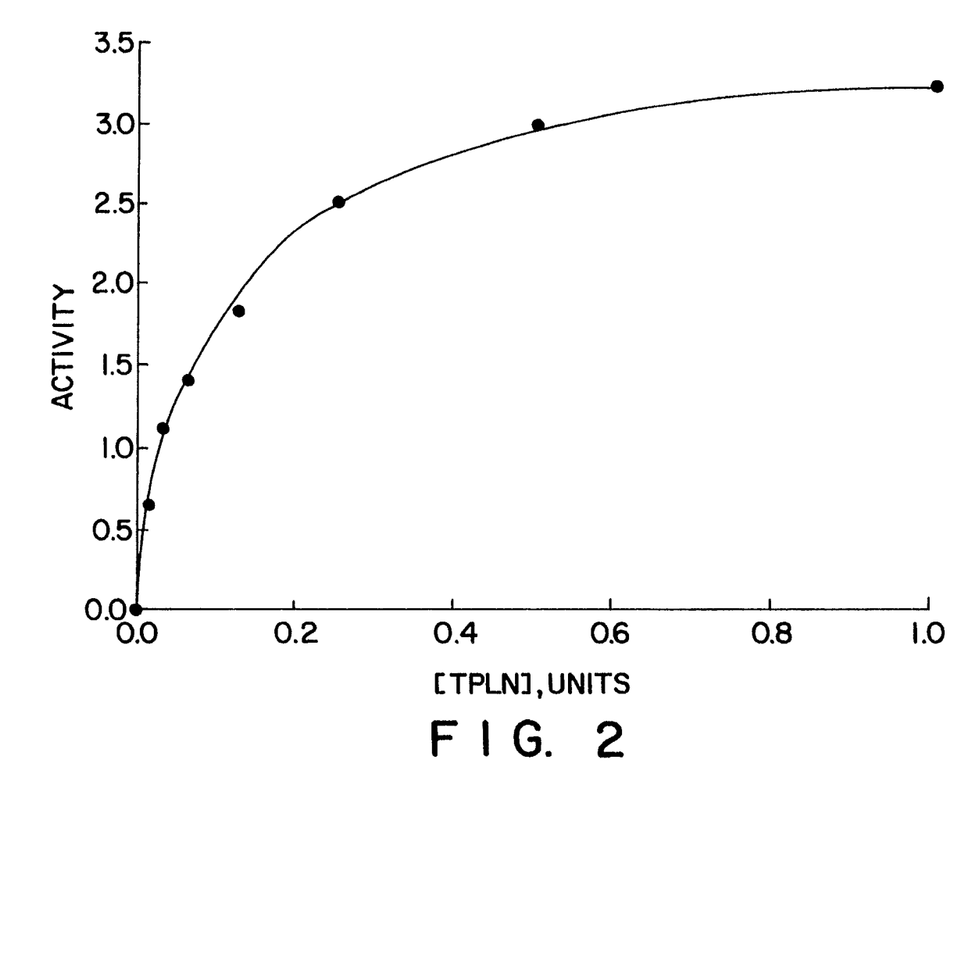
FIG. 2 is a graph of the effect of thromboplastin concentration on the clotting rate.

The maximum rate of change is determined from the progress curve generated and plotted versus the corresponding dilutions. FIG. 1 shows a typical progress curve. The reference thromboplastin was given an arbitrary concentration of 1 Unit. FIG. 2 shows a plot of change in absorbance ($\Delta A$) at 405 nm versus thromboplastin concentration in terms of Units/ml. The data suggests saturation kinetics and can be described using the following equation:

$$\Delta A/min = \Delta [TPLN]/(\beta + [TPLN]) \qquad (1)$$

where [TPLN] is the thromboplastin activity concentration and $\alpha$ and $\beta$ are constants. Equation 1 can be transformed into the following form:

$$1/(\Delta A/min) = \beta/\alpha(1/[TPLN]) + 1/\alpha \qquad (2)$$

Figure 3:
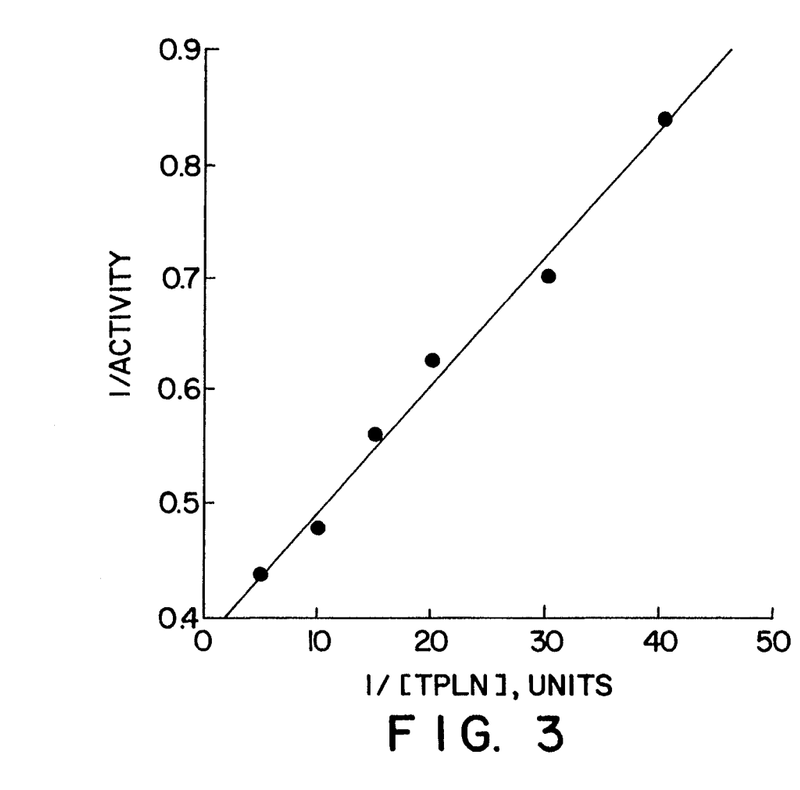
FIG. 3 is a thromboplastin calibration curve.

FIG. 3 shows a plot of 1/[TPLN] versus 1/($\Delta A/min$). Calibration curves such as this were and can be used to estimate the amount of thromboplastin in any extracts obtained.

The process of producing the stable, liquid thromboplastin reagent is generally described as;
a) washing rabbit brain acetone powder extract, allowing the solution to separate and discarding the supernatant;
b) warming the washed extract, and mixing the extract with an extraction solution, while continually heating the solution to about 45° C.;
c) centrifuging the solution;
d) removing the supernatant and adding albumin and calcium ions;
e) incubating the solution;
f) adjusting the pH; and
g) adding preservative, stabilizing and antimicrobial agents.

Figure 4:
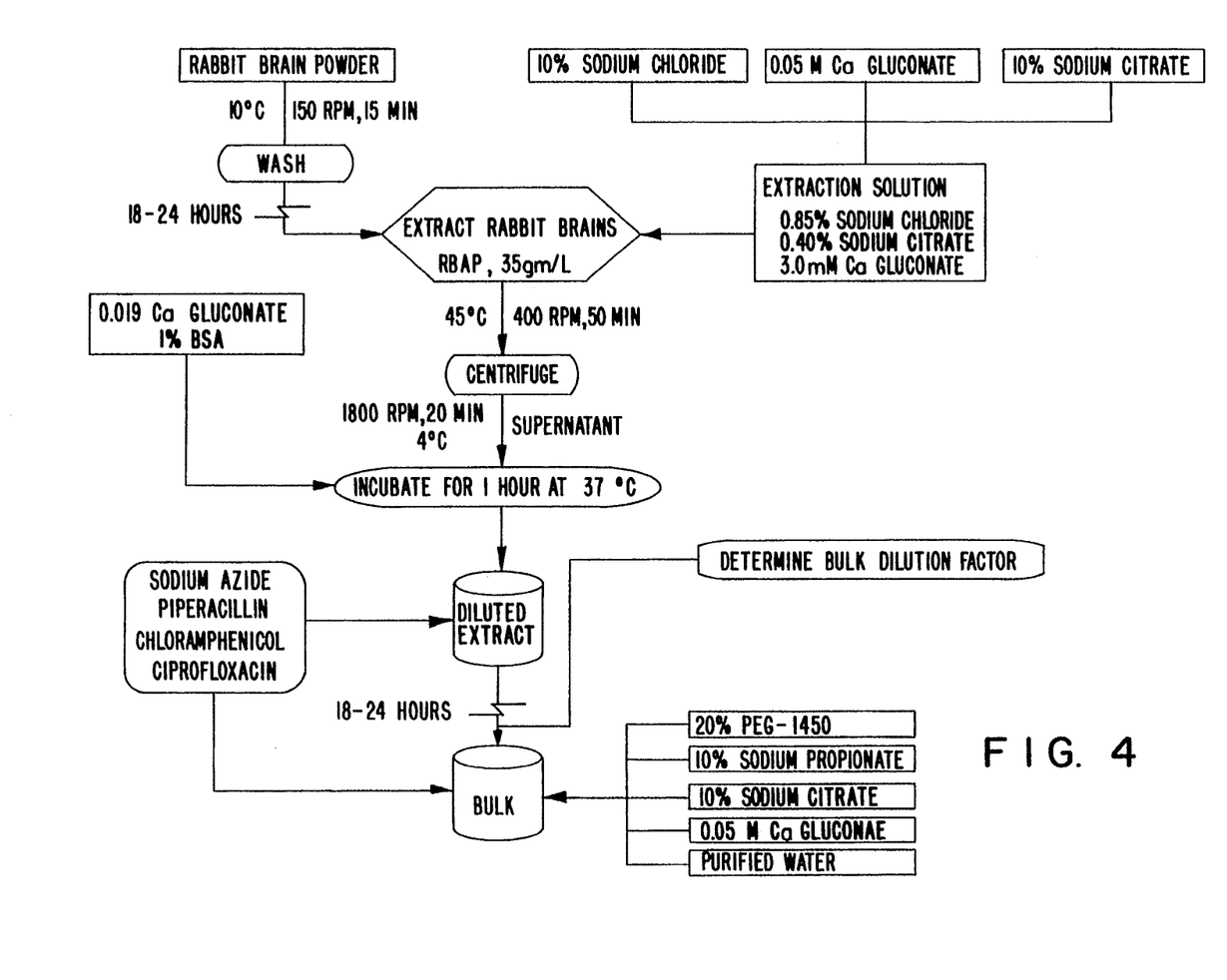
FIG. 4 is a flow diagram of the method of producing liquid thromboplastin reagent.

Specifically, the method of producing the liquid thromboplastin reagent is described below and diagrammed in FIG. 4. The RBAP is initially washed with deionized water, preferably at approximately 10° C., but an acceptable range is about 2° to 12° C., and at a concentration of approximately 28 grams RBAP/L of water. Although 28 gm/L is the preferable concentration, the concentration can range between about 10 and 40 gm of RBAP/L of water. The solution is mixed at approximately 150 RPM for about 15 minutes and allowed to settle overnight at 10° C. The supernatant is discarded.

Washing with water at 2°-8° C. removes only 0.2% of the available thromboplastin activity of the powder. However, significant levels of soluble enzymes such as lipases and proteases, and salts, chromophores, bacteria and particulates are removed under these conditions.

The advantages of washing the RBAP prior to extraction are numerous. First, the wash procedure partially removes dead and viable bacteria, along with dust and other debris. This decontamination results, among other things, in improved optical clarity. Moreover, the wash step minimizes the effect of variations in RBAP particle size since the powder is completely wetted during the overnight settling period. This step also normalizes possible variations in the concentration of soluble salts and proteins in the RBAP because an excess of water is used.

The wet RBAP is warmed to approximately 25° C., and then the Extraction Solution, prewarmed to approximately 45° C. is added The range of RBAP concentrations studied was 25.0 to 40.0 grams per liter of Extraction Solution. The most preferred concentration is 35 grams of RBAP per liter of Extraction Solution. This amount of RBAP resulted in the maximum amount of thromboplastin extracted in one stage. Higher amounts of RBAP (i.e., 40 gm/L) did not produce proportional increases in yield. Lower amounts of RBAP (i.e., <30 gm/L) could jeopardize the reagent during those times of the year when the available rabbit brain powder is of poorer quality. The most preferred concentration of the various components of the Extraction Solution are described in Table 1.

These extraction conditions resulted in the maximum yield of thromboplastin activity. Moreover, these conditions produced the lowest normal clotting time and a sensitivity close to the target achievable prior to the final volume adjustment of the reagent batch, called "bulking".

TABLE 1

| EXTRACTION SOLUTION | |
|---|---|
| COMPONENT | CONCENTRATION (wt/vol) |
| Sodium Chloride | 0.85% |
| Sodium Citrate | 0.40% |
| Calcium Gluconate | 3.0 mM |

Although the preferred concentration of each of the components of the Extraction Solution are given in Table 1 above, an acceptable range for sodium chloride is from about 0.5% to 1.5%; for sodium citrate, from about 0.2% to 0.6%; and for calcium gluconate, from about 2 mM to 6 mM.

Sodium chloride has a significant effect on the yield of thromboplastin obtained. The extraction rate increases proportionately with increasing ionic strength up to a maximum point, after which the rate decreases with further increase in ionic strength. Sodium chloride, while found to be the preferred reagent, can also be replaced by chloride salts of other monovalent metal ions, such as potassium and lithium, with a similar effect.

The level of calcium has a minor role in the yield obtained but has a dramatic effect on the normal range and the sensitivity of the resulting thromboplastin. Calcium gluconate provides the necessary calcium for the coagulation cascade that results in the formation of a clot. Extraction of RBAP in the absence of calcium results in a preparation with low normal plasma clotting times after recalcification, but very poor sensitivity to abnormal patient plasmas. Within certain ranges, using increasing concentrations of calcium in the Extraction Solution, the resulting extract has higher sensitivity to abnormal plasmas and higher normal clotting times.

Previous studies have shown that the stability of thromboplastin is enhanced when calcium is added in the form of the gluconate calcium salt rather than as calcium chloride. Divalent cations, such as calcium and magnesium, can strongly bind membranes, particularly those containing acidic phospholipids.

Binding by calcium and magnesium can bring about vesicle aggregation, the driving force of which is presumably van der Waals interactions. The rate of fusion increases with temperature and membrane fluidity, and is especially rapid at the phase-transition temperature. The improved stability observed with the use of calcium salts of carbohydrate acids, such as gluconate or tartrate, may be attributed to the formation of coordination complexes or through partial sequestration of calcium ions. Surface response optimization studies indicated that the optimum concentration of calcium was 11.0 mM.

Sodium citrate is a weak divalent ion chelator and, thus, modulates the effect of calcium. In other words, citrate sequesters part of the calcium available and reduces its effective concentration. As the extraction proceeds and the calcium is bound by other components being released into solution (i.e., proteins and lipids), the calcium equilibrium is displaced and citrate-bound calcium is released. This process, in practice, maintains a semi-constant concentration of calcium during the extraction. Although sodium citrate and calcium gluconate are considered the preferable compounds in the reagent, other weak metal ion chelators, such as oxalate can be used in place of the sodium citrate, while the calcium ions can also be provided by, for example, calcium tartrate and calcium lactate.

The wet RBAP-Extraction Solution dispersion is then heated to approximately 45° C. while mixing at about 400 RPM for approximately 50 minutes. The extraction rate does not change dramatically when the RPM increases from 100 to 500 RPM. However, the magnitude of the amount extracted with time significantly increases with faster mixing.

The dispersion is then centrifuged at approximately 1800 RPM for 20 minutes at 4° C. These are optimum conditions. Acceptable conditions include centrifuging from 1500 RPM to 2200 RPM for about 15 to 30 minutes at about 2° C. to about 10° C.

The supernatant is rewarmed and diluted at approximately 1:1 with a solution of 1% bovine serum albumin (BSA) and 0.019 M calcium gluconate.

Albumin has multiple roles in this formulation. It is believed that serum albumin helps stabilize lipid vesicle systems by intercalating into lipid bilayers and making them more rigid. In addition, the albumin protects active proteins by masking the action of degradative proteases. A protease-free quality of BSA is required for optimum product stability. The diluted extract is incubated for about 1 hour at 37° C. This incubation period allows for recalcification of the extract and for annealing of vesicles to a thermodynamically favorable state.

After incubation, the extract is cooled to approximately 25° C., pH adjusted to about 6.6, and the stabilizers, antimicrobials and preservatives, if desired, are added.

Although polyethylene glycol (PEG) has a variety of uses in this formulation, one of the uses is as a stabilizer and a preservative. Albumin is also used as a stabilizer, and sodium propionate is used as both.

The degree of bilayer dehydration plays an important role in the induction of vesicular membrane fusion. Strong hydration forces have to be overcome in order to allow membranes to come into close proximity. For this reason, dehydration agents, such as PEG and dextran, can have a significant effect on the fusion rate of phospholipid vesicles.

Hoekstra performed fusion experiments in the presence of PEG that suggests that the degree of bilayer dehydration and the creation of "point defects" in the bilayer are dominant factors in the initial fusion effects. (D. Hoekstra, J. Amer. Chem. Soc., 21, p. 2834, (1982)). PEG, in the absence of calcium or magnesium, can aggregate vesicles without fusion, while PEG in the presence of small amounts of divalent cations (i.e., >0.5 mM) facilitates fusion.

Clearly then, PEG could effect the stability of the thromboplastin formulation. However, PEG does provide an efficient mechanism to modulate normal clotting times and in the adjustment of Factor sensitivities. In addition, PEG improves the dispersion characteristics of the product. The destabilizing effect is minimal at concentrations below 2%.

Studies of the effect of PEG-1450 showed that at concentrations between 0.1% to 5% there was a gradual decrease in PT of all reference plasmas, including Factor VII-deficient plasma and coumadin plasma. In addition, studies of particle size showed considerable changes in the vesicle size, particularly above 2% PEG-1450. Above 2.0% PEG-1450 but below 15%, the size distribution becomes narrower.

Above 15%, PEG-1450 causes a precipitate to form in reference plasmas and this precipitate mimics clot formation in the absence of thromboplastin. This observation indicates that PEG probably shortens PT values by promoting and enhancing the aggregation of fibrin strands during the clotting process.

Sodium propionate is used to adjust the clotting time of the thromboplastin preparation with plasma controls and patient samples, if needed. Generally it has been found that up to 0.4% of sodium propionate can be added to the final thromboplastin reagent formulation. The addition of sodium propionate increases the clotting time of all plasmas. However, the clotting time will increase more dramatically for longer clotting time plasmas (i.e. coumadin plasmas) than for normal plasmas. Sodium propionate is also listed in the Merck Index as a fungicide and mold preventative.

Antimicrobials can also be added to the formulation. For example, in a preferred combination, sodium azide at approximately 0.02% to 0.06% and piperacillin, chloramphenicol and ciprofloxacin, all at about 0.007%–0.015% are added. The antimicrobials are added to reduce or eliminate microbiological contamination, including bacterial and fungal, all of which could adversely affect thromboplastin reagent stability. This is particularly important since thromboplastin cannot be sterile-filtered to remove bacteria due to the vesicle nature of the thromboplastin complex.

The cell walls of living microorganisms will allow passage only to small molecular weight molecules. The macromolecules present in the bacteria environment must be broken down before they can be internalized and digested. Bacteria, particularly those that are gram-positive, secrete various enzymes into their surrounding medium. These enzymes include particularly, proteases, lipases, phospholipases, peptidases, and nucleases. Gram-negative bacteria retain these enzymes between the plasma membrane and the cell wall.

Upon death, the cell wall and membrane of these bacteria will degrade resulting in the release into the environment of the same type of degradative enzymes found in both kinds of bacteria.

The stability of thromboplastin reagents depends substantially on maintaining the integrity of its protein and lipid components. Therefore, the level of bacterial contamination, whether gram-positive or gram-negative, viable or dead, is very significant to shelf-life. In addition, although less pronounced, mold and fungi have a similar effect.

There are numerous sources of bacterial contamination. These can be introduced in the raw materials (e.g., RBAP, calcium gluconate, BSA), the manufacturing process, the in-use environment (i.e., open vial), and transfer mechanisms such as valves, tubing and probes. Because of the variety of bacterial sources, the antimicrobial agents used in this formulation have a dual purpose. First, they must eliminate bacteria and fungi during the manufacturing steps and, secondly, they must preclude contamination while the product is in use for a specified time period.

The characteristics of an optimum combination are broad bacteriostatic and bactericidal action with negligible interactions with the product in terms of performance and appearance. Any antimicrobials providing such protection may be useful in this formulation.

The antimicrobial compounds tested could be classified as a) reactive chemicals such as sodium azide, b) reversible inhibitors, such as dithiothretol, c) antibiotics, such as Spiromycin, and d) membrane disruptors, such as phenol. It appears that, in general, gram-negative bacteria are more detrimental to the reagent than gram-positive bacteria. Therefore, it is critical to eliminate these types of bacteria early on in the processing procedure. Also, chemically reactive compounds, although effective in eliminating bacteria, are detrimental to the long-term stability of liquid thromboplastin reagent as judged from accelerated stability studies. Finally, by removing viable and dead cells, the RBAP wash improves the antimicrobial action of the agents tested.

Pseudomonas maltophilia is a persistent and extremely detrimental strain to liquid thromboplastin. The preferred antimicrobial combination is very effective in eliminating this particular class of microbe. This combination consists of sodium azide, piperacillin, chloramphenicol, and ciprofloxacin. The mode of action of each of these compounds is quite different. Piperacillin inhibits cell wall synthesis. Chloramphenicol inhibits protein syntheses, while ciprofloxacin inhibits DNA replication. Sodium azide interferes with the cytochrome system and also has some anti-fungal properties.

A number of antibacterial and antifungal agents were screened to find the most effective combinations. Some alternatives available include the following.

The penicillin family of antibiotics also include the acylaminopenicillins, which include piperacillin, azlocillin and mezlocillin. These antibiotics have increased activity against many gram-negative organisms present in the RBAP and manufacturing environment. They are also able to inhibit the beta-lactamases of Klebsiella pneumoniae, a common microorganism. Spiromycin may also be substituted for piperacillin.

Sodium azide is an effective and inexpensive anti-fungal agent. Clotrimazole, 5-fluorocytosine and nystatin are also effective as fungicides.

Quinolones, such as ciprofloxacin and norfloxacin are also broad based antimicrobials. Gentamycin, streptomycin and amikacin may also serve as replacements for the quinolones.

Chloramphenicol is an inhibitor of protein synthesis. Tetracycline could be used as an alternative, although we have found that this would require higher concentrations of the remaining three antibiotics.

The extract containing the antimicrobials is pH adjusted to approximately pH 6.6 and is maintained at about 2°–8° C. overnight This incubation is used to lower the microbial load quickly.

Once the extract has been fully prepared, the variability of the RBAP must be controlled. The reasons for this variability are numerous and include, for example, hormonal changes in the rabbits during the year. This situation results in some extracts being "richer" in thromboplastin than others and, eventually, reflects in the performance characteristics of the final reagent.

We have used a thromboplastin assay to determine thromboplastin concentrations. A series of dilutions of a reference thromboplastin lot are first prepared using a defined sample buffer, which contains calcium gluconate, sodium chloride, and HEPES buffer, pH 7. The clotting rate of normal plasma is determined using these dilutions from clotting curves generated at 405 nm (i.e., maximum $\Delta A/min$). A dilution of an unknown thromboplastin is analyzed in the same way and the concentration is determined in relation to the reference lot from the calibration curve. This procedure effectively normalizes the thromboplastin concentration to off-set the variation in RBAP encountered.

The preferred final concentrations of all thromboplastin reagent components is shown in Table 2.

TABLE 2

LIQUID THROMBOPLASTIN REAGENT; FINAL FORMULATION

| Component | Concentration (wt/volume) |
|---|---|
| RBAP | From Extract |
| Calcium Gluconate | 11.0 mM |
| PEG-1450 | 1.50% |
| Sodium Chloride | 0.25% |
| Sodium Citrate | 0.20% |
| Bovine Serum Albumin | 0.30% |
| Sodium Propionate | 0–0.5% |
| Sodium Azide | 0.03% |
| Piperacillin | 0.008% |
| Chloramphenicol | 0.006% |
| Ciprofloxacin | 0.006% |

As shown in Table 2, the components of the final formulation are calcium gluconate, sodium citrate, sodium chloride, PEG-1450, bovine serum albumin, sodium propionate and RBAP extract. The formulation also includes a combination of four antimicrobial compounds.

The tolerance of the formulation for variability in the concentration of components is approximately ±5% for each constituent. The components whose concentration impact the performance of the liquid thromboplastin the most are sodium citrate, sodium propionate, and sodium chloride.

The pH of liquid thromboplastin reagent is preferably adjusted to 6.6±0.19.

The final concentration obtained provides the formulation with good sensitivity towards coumadinized patient plasmas. Other factors in the formulation, such as sodium propionate, PEG-1450, calcium gluconate and thromboplastin concentration all contribute to the final sensitivity of the reagent.

The following examples are given to further explain the invention, and are not meant to narrow the invention in any way.

EXAMPLES

The following reagents were used throughout the examples:
1. Rabbit Brain Acetone Powder
   Rabbit brain acetone powder
2. Extraction Solution Components
   D-gluconic acid/hemicalcium salt—stock solution of 0.05M (Sigma Chemical Co., St. Louis, Mo. USA)
   Sodium chloride, USP Granular
   Sodium citrate, dihydrate—stock solution of 10%
3. Bulk Solution Components
   Polyethylene glycol-1450—stock solution of 20% (J. T. Baker Chemical Co., Buffalo Grove, Ill., USA)
   Bovine serum albumin (BSA)
   Propionic acid, sodium salt—stock solution of 10%
   Sodium azide
   Chloramphenicol
   Ciprofloxacin
   Piperacillin
4. Controls
   Normal pool plasma (NPP)
   Verify ® Normal Citrate plasma control-VNC (Verify is a trademark of Organon Teknika Corporation, Durham, N.C., USA).
   Verify ® Abnormal Citrate Level I (VACI)—abnormal plasma
   Verify ® Abnormal Citrate Level II (VACII)—abnormal plasma
   Verify ® 1—normal plasma control
   Verify ® 2 and 3 (abnormal plasma controls)

EXAMPLE 1

Preparation of Liquid Thromboplastin Reagent

Rabbit brain acetone powder was washed with deionized water at 10° C. at a concentration of 28 g RBAP/L $H_2O$. The RBAP was washed by mixing at 150 RPM for 15 minutes. The wet RBAP settled overnight at 10° C. The supernatant was removed by suction and discarded. The wet RBAP was warmed to 25° C. and an extraction solution, prewarmed to 45° C., was added. The extraction solution consisted of an aqueous solution of 0.85% sodium chloride, 0.40% sodium citrate and 3.0 mM calcium gluconate. The dispersion was heated to 45° C. while mixing at 400 RPM for 50 minutes. The extract was then centrifuged at 1800 RPM for 20 minutes at 4° C., and the supernatant removed.

The supernatant was diluted 1 to 1 with a solution of 1% BSA and 0.019M calcium gluconate and incubated for 1 hour at 37° C. The diluted extract was then cooled to 25° C. and 0.05% sodium azide, 0.01% piperacillin, 0.01% chloramphenicol, and 0.01% ciprofloxacin was added. The diluted extract was pH adjusted to 6.65 and refrigerated overnight at 2°–8° C.

In order to minimize the effects of variability of various lots of RBAP, the concentration of the thromboplastin in the diluted extract was typically determined using a simplified procedure called the Bulk Dilution Factor (BDF). To obtain the BDF, a series of small-scale dilutions are prepared from the diluted extract. For example, the final concentration of each of the bulking components, as seen in Table 2, is maintained constant in six flasks, while varying amounts of thromboplastin-Extraction Solution are added, and then each flask is diluted with water to a constant volume. The preferred final concentrations of thromboplastin range from 1.4- to 1.9-fold. Effectively, only the thromboplastin concentration changes from solution to solution. The solutions are then analyzed for PT values using normal pool plasma, control plasmas, Factor VII-deficient plasma, and various coumadin treated patient plasmas. The optimum BDF (i.e., optimum thromboplastin concentration) is chosen from the results obtained.

If optimum performance values cannot be obtained, a second set of test solutions are prepared using the best BDF previously obtained and various concentrations of sodium propionate. Having the flexibility of adjusting the diluted extract with both the BDF and sodium propionate minimize the impact of variability of the RBAP.

The final composition of the liquid thromboplastin reagent prepared was 11.0 mM calcium gluconate, 1.5% PEG-1450, 0.25% sodium chloride, 0.2% sodium citrate, 0.3% BSA, 0-0.5% sodium propionate (variable), 0.03% sodium azide, 0.008% piperacillin, 0.006% chloramphenicol and 0.006% ciprofloxacine.

EXAMPLE 2

Extraction Temperature and Time

Studies on the effect of time and temperature on the extraction efficiency were done at 37° C. 42° C. 45° C. 47° C. and 50° C.

At each of the five temperatures studied, a jacketed 600 ml vessel was used to prepare the water bath. 200 ml centrifuge tubes were used as reaction vessels. A circulating water bath was used for temperature control. The Extraction Solution was continuously mixed with an overhead stirrer set at 500 RPM.

The Extraction Solution was placed in the reaction vessel and allowed to equilibrate to temperature for 0.5 hours with stirring. 20 grams of RBAP was then sprinkled into the solution. The solution was continuously stirred at 750 RPM. Aliquots of 10 ml were removed at time intervals (10, 20, 30, 60, 90, 120 minutes, etc. up to 24 hours).

The aliquots were centrifuged at 5° C., 1800 RPM for 20 minutes. The supernatant of each sample was transferred to 10 ml glass vials and analyzed for thromboplastin activity.

Figure 5:
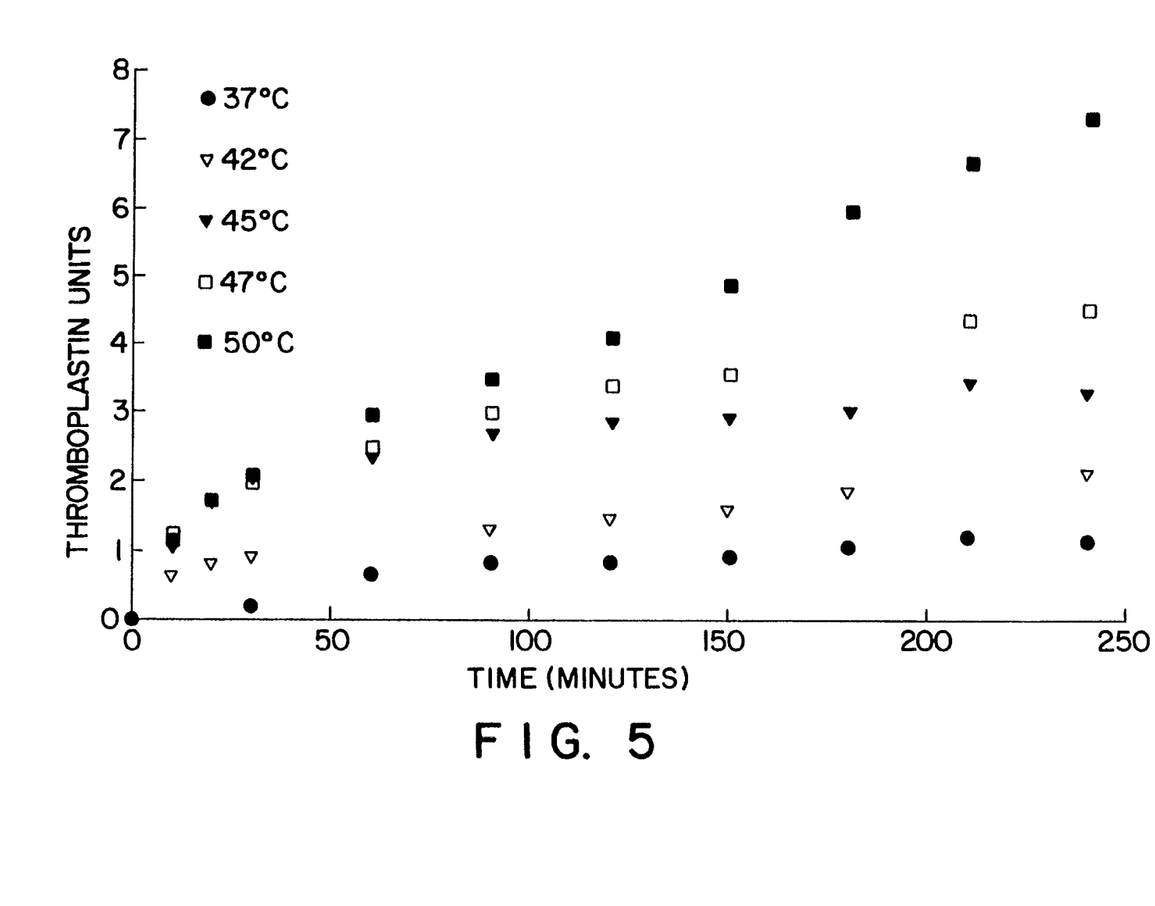
FIG. 5 is a rabbit brain acetone powder extraction isotherm graph.

FIG. 5 shows the amount of thromboplastin (Units per ml) extracted as a function of time and temperature. FIG. 5 shows that after an initial 25-50 minute period, the amount of thromboplastin extracted is a linear function of time at all temperatures. The initial non-linear portion of the extraction curves probably corresponds to the wetting of the RBAP.

A surface-response curve was generated obtaining a mathematical relationship between the amount of thromboplastin (TPLN) extracted with respect to time and temperature. The data gave a good fit to a cubic model as judged by the standard deviation and the influence parameters obtained. The equation is as follows:

$$2.1T^2t + 2.5t + 0.70^2 - 0.60t^2 + 3.5T + 1.6t + 2.0 \quad (3)$$

where T is temperature and t corresponds to time. FIG. 5 also shows that the amount of TPLN extracted increases with extraction temperature.

A simple mathematical model was derived relating the extraction temperature to the amount of TPLN extracted. The model is based on the fact that the chemical potential, $\mu$, of the TPLN at equilibrium should be constant in both phases:

$$\mu(RBAP) = \mu(B) \quad (4)$$

$$\mu^0(RBAP) + RT \ln y = \mu^0(B) + RT \ln x \quad (5)$$

where the $\mu^0$s are chemical potentials in standard reference states, B is the extraction buffer, x is the TPLN concentration in the extraction buffer, y is the TPLN concentration in the RBAP, and R is the universal gas constant. The model assumes that after 4 hours of extraction, the system approximates equilibrium. FIG. 5 shows that this is an acceptable assumption, except perhaps at 50° C. where the extraction rate is high and, also, where a secondary mechanism may be in effect.

Figure 6:
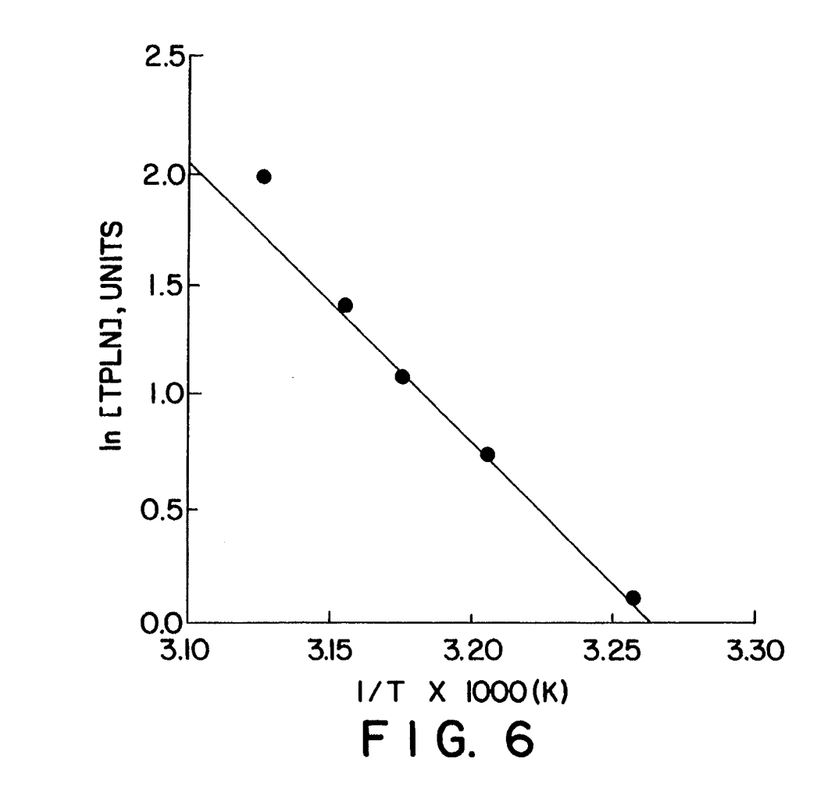
FIG. 6 is a plot of absolute temperature versus the amount of thromboplastin extracted at equilibrium.

Equation 5 can be transformed into the following form:

$$\ln K = \sigma/R \, (1T) \quad (6)$$

where K is the partition coefficient (x/y) and $\sigma$ is a combination of constants. FIG. 6 shows a plot of 1/T versus the logarithm of the extracted thromboplastin in units. With the exception of the point corresponding to 50° C., the points fit a linear relationship as predicted from the model.

The deviation from the model at 50° C. emphasizes the considerably different amount of thromboplastin extracted at this temperature. Table 3 shows a comparison of the extraction rate at different temperatures.

TABLE 3

| Extraction Rate of RBAP at Various Temperatures | |
|---|---|
| Temperature | Extraction Rate (mUnits/min) |
| 37.0 | 2.67 |
| 42.0 | 5.40 |
| 45.0 | 5.14 |
| 47.0 | 11.3 |
| 50.0 | 25.6 |

The enhanced extraction between 47° C. and 50° C. may indicate that this is the temperature region corresponding to the Critical Temperature (Tc) of the lipids in the suspension. Above the Tc, lipid vesicles are more fluid and, therefore, disperse more efficiently. Below the Tc, the vesicles are more rigid and the extraction is decreased. Table 3 shows that the extraction rate changes very little in the 42° C. to 45° C. region. In this temperature region lot-to-lot variability would be minimized.

EXAMPLE 3

Mixing Conditions

Studies were done on the effect of mixing speed on the extraction rate of RBAP.

Experiments were performed at 100, 175, 250, 350 and 500 RPM as follows:

1000 ml of the Extraction Solution, as described in Example 1, was placed in a 2 liter stainless steel Dewar flask (10.5 cm diameter × 31 cm height) and allowed to warm to the extracting temperature of 45° C. The temperature in the tank was monitored. 20 grams of RBAP was sprinkled on top of the extracting solution without stirring. Time zero was defined as the activation of the stirrer at each of the above RPM settings. Samples were removed every ten minutes and centrifuged at 1200 RPM for 3 minutes. The supernatant was diluted with buffer and refrigerated. The diluted samples were analyzed for thromboplastin concentration using the thromboplastin assay described above.

The results obtained indicated that the extraction rate did not change dramatically with increasing mixing speed. On the other hand, the magnitude of the amount extracted with time significantly increased with faster mixing.

Figure 7:
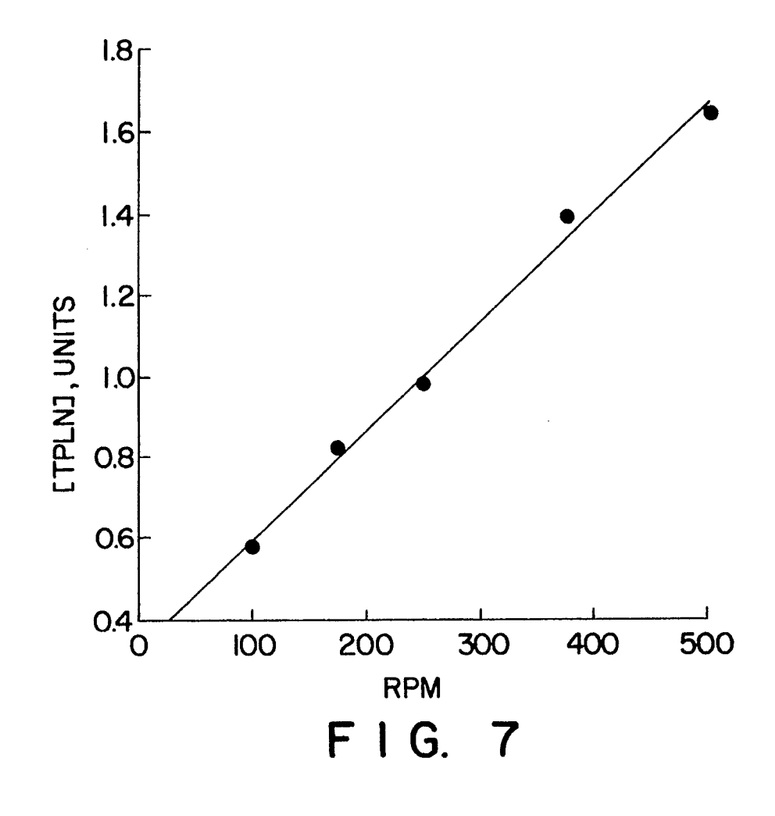
FIG. 7 is a graph of the effect of mixing speed on the extraction of rabbit brain acetone powder.

Faster mixing shifts the total amount extracted to higher values without considerably affecting the slopes of the curves. FIG. 7 shows the amount of thromboplastin extracted at 45° C. after 60 minutes at different mixing speeds. FIG. 7 shows that there is a linear relationship between the amount of thromboplastin extracted and the mixing speed.

EXAMPLE 4

Effect of Ionic Strength on Thromboplastin Extraction from RBAP

RBAP (0.15 g) was placed in 8-5ml plastic test tubes. A stock 1M NaCl solution was prepared and 3 ml of NaCl solution (corresponding to a molarity of 0 to 1M) were added to each tube. The tubes were vortexed for 5 seconds each and placed in a 45° C. water bath. After a 10 minute incubation, the tubes were vortexed for 5 seconds and replaced in the water bath for an additional 5 minutes. At the end of the 15 minute period, the tubes were centrifuged at 1800 RPM for 20 minutes at 4° C. The supernatant was then diluted 30-fold in buffer and analyzed for thromboplastin concentration. The NaCl concentration was converted to ionic strength.

Figure 8:
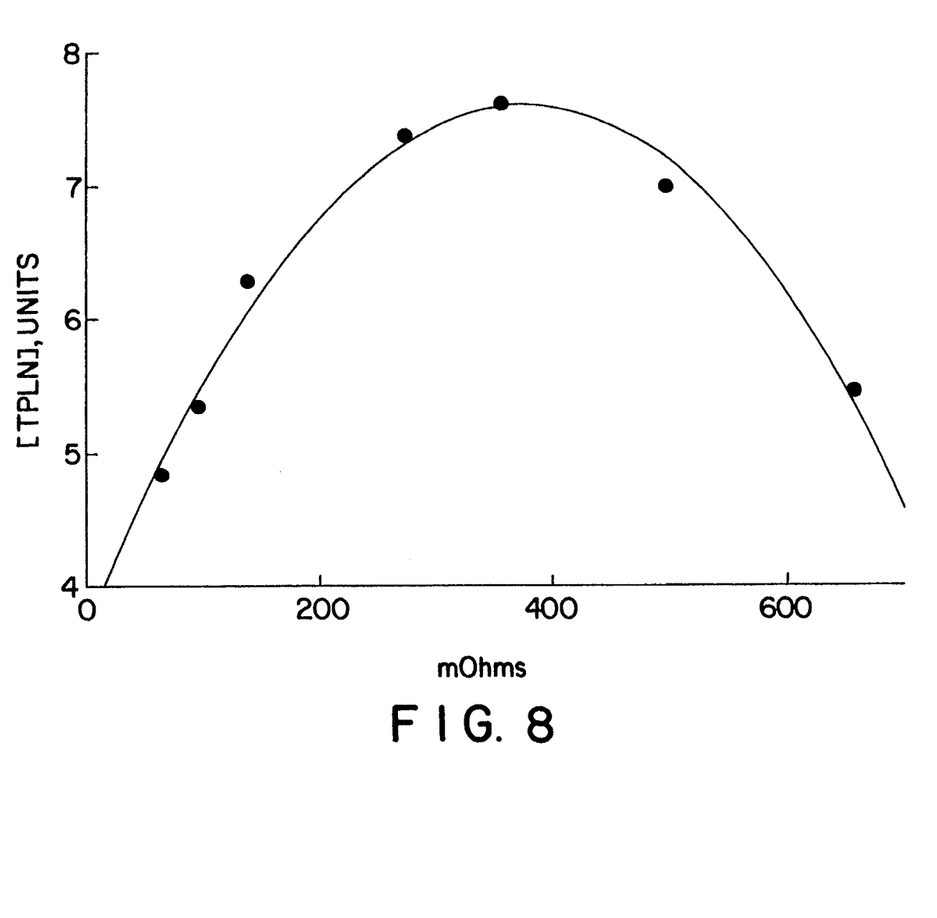
FIG. 8 is a plot of the effect of ionic strength on the extraction of rabbit brain acetone powder.

FIG. 8 shows a plot of the amount of thromboplastin activity obtained as a function of ionic strength in the extraction buffer. FIG. 8 shows that the extraction rate increases with increasing ionic strength up to a maximum point, after which the rate decreases with further increase in ionic strength.

One possibility for the existence of a maximum point is that the ionic strength also accelerates the rate of sedimentation during centrifugation. Therefore, the augmented sedimentation rate will result in an apparent reduction in the extraction rate since the samples are analyzed for the TPLN concentration using the supernatant after centrifugation of the extract.

EXAMPLE 5

Obtaining Optimum Thromboplastin Concentration for Reagent

A vial of extracted thromboplastin was diluted with buffer up to 32 times and the various dilutions were assayed using normal pool plasma (NPP), and plasma controls Verify® Normal Citrate (VNC), and Verify® Abnormal Citrate Levels I and II (VACI and VACII). The thromboplastin concentrations were determined on the dilutions.

Figure 9:
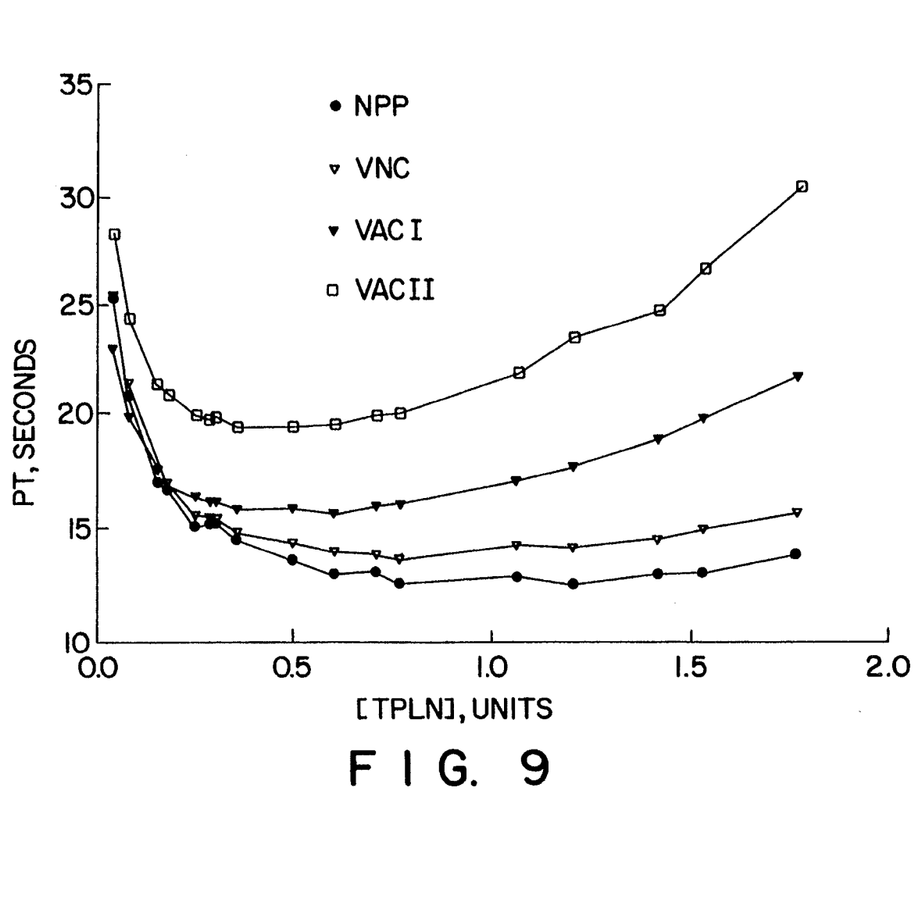
FIG. 9 shows the effect of thromboplastin concentration on the clotting time of various control plasmas.

FIG. 9 shows a plot of the effect of TPLN concentration on clotting time using NPP, Verify® Normal Citrate, and Verify® Abnormal Levels I and II. FIG. 9 shows typical saturation curves in the case of NPP and VNC, with a slight increase in values at high TPLN concentrations. In the case of the abnormal plasmas, however, the values increase considerably with increasing TPLN concentration. This effect is also observed with Factor VII-deficient plasma and coumadinized patient plasma.

These data indicate that when the extraction conditions result in a TPLN of approximately 1.5 Units, small departures from the target would produce considerable changes in the performance characteristics. In addition, during long-term storage, small decreases in TPLN concentration would be very noticeable in terms of clotting times. On the other hand, TPLN values in the 0.5 to 1.0 Unit range accommodate TPLN variability much better and should result in preparations with higher long-term stability.

EXAMPLE 6

Performance Characteristics of Liquid Thromboplastin Reagent

As observed in Table 4, the four research lots (RL1–RL4), prepared as in Example 1, give results similar in various tests as compared to an industry standard thromboplastin reagent, Simplastin Excel, and generally exhibit very good reproducibility from lot-to-lot.

TABLE 4

| SUMMARY OF RESULTS FROM RESEARCH LOTS | | | | | |
|---|---|---|---|---|---|
| Specification | Simplastin Excel | RL1 | RL2 | RL3 | RL4 |
| Bacteria Level | $4.4 \times 10^3$ | 0 | 0 | 0 | 0 |
| Mold | 0 | 0 | 0 | 0 | 0 |
| Normal Mean | 12.0 | 12.0 | 12.3 | 12.4 | 12.0 |
| VNC | 12.4 | 12.3 | 12.6 | 12.5 | 12.2 |
| VACI | 18.8 | 18.1 | 18.2 | 18.5 | 18.5 |
| VACII | 29.6 | 26.8 | 26.7 | 27.4 | 27.9 |
| Verify 1 | 11.0 | 11.4 | 11.7 | 11.6 | 11.6 |
| Verify 2 | 16.8 | 16.3 | 16.5 | 16.6 | 17.2 |
| Verify 3 | 23.1 | 21.5 | 21.6 | 22.1 | 23.8 |
| ISI | 2.04 | 2.06 | 1.97 | 2.05 | 2.06 |
| Factor Sensitivity | | | | | |
| V | — | 31 | 35 | 40 | 37 |
| VII | — | 33 | 37 | 33 | 33 |
| X | — | 34 | 34 | 33 | 31 |
| Acceptable SD | | | | | |
| VNC | 0.13 | 0.07 | 0.13 | 0.13 | |
| VACI | 0.21 | 0.12 | 0.09 | 0.07 | |
| VACII | 0.60 | 0.22 | 0.24 | 0.33 | |
| Acceptable CV (%) | | | | | |
| VNC | 1.09 | 0.61 | 1.08 | 1.02 | |
| VACI | 1.13 | 0.69 | 0.49 | 0.39 | |
| VACII | 2.16 | 0.88 | 0.94 | 1.24 | |

Additionally, Table 5 summarizes similar results for another five lots of liquid thromboplastin reagent also prepared as in Example 1 (Verify® 1, 2 and 3 are used as control plasmas). These five development lots were prepared as in Example 1. The lot-to-lot reproducibility seen is a result of the process as taught in this specification together with stabilizers and antimicrobial agents.

TABLE 5

| PERFORMANCE RESULTS OF THROMBOPLASTIN REAGENT DEVELOPMENT LOTS | | | | | |
|---|---|---|---|---|---|
| | TEST | | | | |
| | 1 | 2 | 3 | 4 | 5 |
| BDF* | 1.6 | 1.6 | 1.6 | 1.6 | 1.6 |
| Propionate | 0 | 0 | 0 | 0.1 | 0.1 |
| Verify 1 | 11.7 | 11.3 | 11.6 | 11.2 | 11.4 |
| Verify 2 | 17.5 | 17.2 | 16.9 | 17.2 | 17.5 |
| Verify 3 | 25.7 | 25.0 | 25.9 | 25.8 | 25.1 |
| Bacteria | 0 | 0 | 0 | 0 | 0 |
| Mold | 0 | 0 | 0 | 0 | 0 |
| CV | | | | | |
| Verify 1 | 1.20 | 0.51 | 0.90 | 0.90 | 1.0 |
| Verify 3 | 0.93 | 0.23 | 1.00 | 0.40 | 1.2 |
| Normal Mean | 12.1 | 12.2 | 12.1 | 11.7 | 11.6 |
| ISI | 2.03 | 2.03 | 1.96 | 1.95 | 2.02 |

*BDF - Bulk Dilution Factor

EXAMPLE 7

Optimized ISI Value for Liquid Thromboplastin Reagent

The International Sensitivity Index (ISI) is an empirically determined calibration value which reflects the oral anticoagulant sensitivity of a thromboplastin reagent when compared to the World Health Organization International Reference preparation. ISI values of the liquid reagent prepared as in Example 1 were determined using a reference lot calibrated against the World Health Organization International Reference.

A series of coumadinized patient plasmas and normal plasmas were analyzed with the test thromboplastin reagent and the reference thromboplastin reagent for PT values. The log-log orthogonal regression of a plot of the PT's of the reference versus the test was obtained. The slope of the regression line, when multiplied by the ISI of the reference reagent, yields the ISI of the test reagent. The tightly obtained results for five liquid thromboplastin reagent development lots are shown in Table 5, and for four research lots of liquid thromboplastin reagent in Table 4.

EXAMPLE 8

Stability of Liquid Thromboplastin Reagent

A. Closed Vials

One lot of liquid thromboplastin reagent was prepared similarly as described in Experiment 1, and contained RBAP, PEG-1450, BSA, sodium citrate, sodium chloride, calcium gluconate, sodium azide, and thimerosal. Samples of this lot have been stored at 2°–8° C. for 24 months. PT tests were run on duplicates of this lot and are shown in Table 6. The results show that the PT results at 20 months are comparable between the industry standard, Simplastin Excel, and this lot, and that the lot gave similar results at 0 months and at 20 months.

TABLE 6

CLOSED VIAL STABILITY PT RESULTS (SECONDS)

| | MONTH | | | | | | |
|---|---|---|---|---|---|---|---|
| | 0 | 3 | 6 | 9 | 12 | 18 | 20 |
| EXPERIMENTAL LOT (1.2% PROPIONIC ACID) | | | | | | | |
| VNC | 11.9 | 12.6 | 12.3 | 12.0 | 12.3 | 12.8 | 12.8 |
| VACI | 19.5 | 18.8 | 20.3 | 20.0 | 19.4 | 19.8 | 18.7 |
| VACII | 30.1 | 30.3 | 30.1 | 33.0 | 29.6 | 30.9 | 30.3 |

| | MONTH | | | | | |
|---|---|---|---|---|---|---|
| | 0 | 3 | 6 | 12 | 18 | 20 |
| SIMPLASTIN EXCEL | | | | | | |
| VNC | 12.5 | 12.9 | 12.0 | 12.3 | 12.7 | 12.8 |
| VACI | 19.2 | 17.8 | 20.8 | 19.3 | 18.7 | 18.7 |
| VACII | 28.5 | 27.2 | 30.9 | 29.6 | 29.5 | 30.3 |

Additionally, the research lots as described in Example 6 have been tested for actual stability at 2–8° C. for up to 12 months. The results are given below in Table 7, showing the reagent performs within aceptable limits as defined by the control plasmas, VNC, VACI and VACII.

TABLE 7

CLOSED VIAL STABILITY RESEARCH LOTS PT RESULTS (SECONDS)

| | MONTH | | | | |
|---|---|---|---|---|---|
| | 0 | 3 | 6 | 10 | 12 |
| RL1 | | | | | |
| VNC | 12.3 | 11.9 | 12.8 | N/A | N/A |
| VACI | 18.1 | 18.1 | 18.1 | 18.2 | 18.1 |
| VACII | 26.5 | 26.5 | 27.7 | 27.7 | 27.9 |
| Simp. Excel | | | | | |
| VNC | 12.4 | 12.3 | 12.9 | N/A | N/A |
| VACI | 18.5 | 18.1 | 18.8 | 18.5 | 17.8 |
| VACII | 29.4 | 29.6 | 33.2 | 30.0 | 28.9 |
| RL2 | | | | | |

TABLE 7-continued

CLOSED VIAL STABILITY RESEARCH LOTS PT RESULTS (SECONDS)

| | | | | | |
|---|---|---|---|---|---|
| VNC | 12.6 | 12.5 | 12.5 | N/A | N/A |
| VACI | 18.3 | 17.6 | 18.2 | 18.1 | 18.6 |
| VACII | 26.1 | 26.9 | 27.4 | 27.1 | 28.2 |

| | MONTH | | | | |
|---|---|---|---|---|---|
| | 0 | 3 | 6 | 9 | 11 |
| RL3 | | | | | |
| VNC | 12.5 | 12.5 | 12.5 | N/A | N/A |
| VACI | 18.7 | 17.6 | 18.2 | 18.1 | 18.6 |
| VACII | 27.7 | 26.9 | 27.4 | 27.1 | 28.2 |

| | 0 | 3 | 9 | 10 |
|---|---|---|---|---|
| RL4 | | | | |
| VNC | 12.2 | 12.6 | N/A | N/A |
| VACI | 18.5 | 17.9 | 17.9 | 17.6 |
| VACII | 27.9 | 27.8 | 27.7 | 27.2 |

B. Opened Vials

Six opened vials of the lots of liquid thromboplastin reagent as described in Example 6, Research Lots 1–3 and Developments Lots DL 1–3, show a stability of at least 14 days in Table 8 below, when measured by their performance in a PT test.

TABLE 8

OPENED VIAL STABILITY-PT RESULTS (SECONDS)

| | Day 0 | Day 7 | Day 14 |
|---|---|---|---|
| RL 1 | | | |
| VNC | 12.4 | 12.5 | 12.2 |
| VACI | 18.4 | 18.7 | 18.2 |
| VACII | 27.4 | 27.8 | 26.9 |
| RL 2 | | | |
| VNC | 12.2 | 12.2 | 12.4 |
| VACI | 18.2 | 18.3 | 18.3 |
| VACII | 26.5 | 26.6 | 26.7 |
| RL 3 | | | |
| VNC | 12.4 | 12.4 | 12.1 |
| VACI | 18.8 | 18.8 | 18.9 |
| VACII | 28.1 | 28.5 | 28.1 |
| DL1 | | | |
| Verify 1 | 11.8 | 11.7 | 11.3 |
| Verify 2 | 17.6 | 17.6 | 17.1 |
| Verify 3 | 24.0 | 24.1 | 24.8 |
| DL2 | | | |
| Verify 1 | 11.8 | 11.6 | 11.3 |
| Verify 2 | 17.4 | 17.4 | 17.0 |
| Verify 3 | 25.7 | 25.2 | 24.7 |
| DL3 | | | |
| Verify 1 | 11.0 | 11.0 | 11.5 |
| Verify 2 | 16.7 | 16.7 | 16.8 |
| Verify 3 | 24.6 | 24.8 | 24.3 |

We claim:

1. A liquid thromboplastin reagent comprising an aqueous solution of rabbit brain acetone powder, calcium gluconate, polyethylene glycol, sodium chloride, sodium citrate, bovine serum albumin, sodium propionate, sodium azide, piperacillin, chloramphenicol and ciprofloxacin, having a shelf life of greater than one month in a sealed container.

2. A method of producing liquid thromboplastin reagent comprising:
   a) washing rabbit brain acetone powder (RBAP) extract with water at a concentration from about 10 to 40 grams of rabbit brain acetone powder (RABR) extract/L
   b) warming the washed extract to about 25° C.;
   c) mixing the warmed extract with an extraction solution while continually heating at about 45° C.;

d) centrifuging the solution at a temperature from about 2° C. to about 10° C.;
e) diluting the supernatant from step of with albumin and calcium ions;
f) incubating the diluted supernatant;
g) adjusting the pH to approximately neutral and adding antimicrobials;
h) adding polyethylene glycol from about 0.1% to 5%;
i) testing the solution for prothrombin time values, and, if needed;
j) adding sodium propionate.

3. A method according to claim 2, wherein said extraction solution comprises sodium chloride, sodium citrate and calcium gluconate.

4. A method according to claim 4, wherein additionally prior to adding sodium propionate, the solution is adjusted by a Bulk Dilution Factor to produce an optimum thromboplastin concentration.

5. A method of producing liquid thromboplastin reagent comprising:
a) cleaning the rabbit brain acetone powder (RBAP) to remove extraneous, primarily non-thromboplastin containing matter;
b) extracting the thromboplastin from the cleaned rabbit brain acetone powder by (RBAP) mixing with extraction solution at temperatures that are conducive to extraction of thromboplastin;
c) diluting the thromboplastin-containing supernatant from step b with albumin and calcium ions under conditions favorable to the formation of stable vesicles or micelles;
d) stabilizing the solution of step c) further by adjusting the pH;
e) adding antimicrobial agents to the solution;
f) additionally stabilizing the solution by adding polyethylene glycol;
g) testing the solution for prothrombin time (PT) values, and, if needed;
h) adjusting the prothrombin time values.

6. A method according to claim 5, wherein additionally after testing the solution for prothrombin time values, the solution is adjusted by a Bulk Dilution Factor to produce an optimum thromboplastin concentration.

7. A method according to claim 5, wherein the prothrombin time values are adjusted by the addition of sodium propionate.

* * * * *

UNITED STATES PATENT AND TRADEMARK OFFICE
CERTIFICATE OF CORRECTION

PATENT NO. : 5,358,853
DATED : October 25, 1994
INVENTOR(S) : James R. Butler, Juan L. Torres and Rajesh Sharma It is certified that error appears in the above-indentified patent and that said Letters Patent is hereby corrected as shown below:

On the title page item [73], delete " Akzo AV" and insert --Akzo N.V.--.

Column 16, line 65, delete "(RABR)" and replace with -- (RBAP) --.

Coulmn 17, line 3, delete "of" and replace with -- (d) --.

Column 17, line 16, delete "4" and replace with -- 2 --.

Signed and Sealed this

Twenty-fifth Day of April, 1995

Attest:

BRUCE LEHMAN

*Attesting Officer*     *Commissioner of Patents and Trademarks*